(12) United States Patent
Yamaguchi et al.

(10) Patent No.: US 7,858,661 B2
(45) Date of Patent: Dec. 28, 2010

(54) PROTEIN REFOLDING AGENT AND REFOLDING METHOD

(75) Inventors: Shunichiro Yamaguchi, Kyoto (JP); Shuji Miura, Kyoto (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 195 days.

(21) Appl. No.: 12/063,443

(22) PCT Filed: Aug. 11, 2006

(86) PCT No.: PCT/JP2006/315926

§ 371 (c)(1),
(2), (4) Date: Mar. 19, 2008

(87) PCT Pub. No.: WO2007/020886

PCT Pub. Date: Feb. 22, 2007

(65) Prior Publication Data

US 2009/0111971 A1    Apr. 30, 2009

(30) Foreign Application Priority Data

Aug. 16, 2005  (JP) .............................. 2005-235980
Nov. 2, 2005   (JP) .............................. 2005-320200
Nov. 2, 2005   (JP) .............................. 2005-320209
Nov. 7, 2005   (JP) .............................. 2005-322642

(51) Int. Cl.
*A61K 31/19*     (2006.01)
*C07C 61/12*     (2006.01)

(52) U.S. Cl. ..................................... 514/557; 562/512

(58) Field of Classification Search ................ 558/208; 562/512; 560/129, 180; 514/557
See application file for complete search history.

(56) References Cited

FOREIGN PATENT DOCUMENTS

| | | |
|---|---|---|
| JP | 2004-512343 | 4/2004 |
| JP | 2004-528266 | 9/2004 |
| JP | 2004-535366 | 11/2004 |
| WO | WO 01/76638 | 10/2001 |
| WO | WO 02/34791 | 5/2002 |
| WO | WO 02/059146 | 8/2002 |

OTHER PUBLICATIONS

Corday et al., 1964, CAS: 61:87131.*
(2) Darensburg et al., 1995, CAS: 122:314219.*
Chen et al. , 2004, CAS: 141:379203.*
Crandall et al., 1999, CAS: 131:175090.*
He et al., 2003, CAS: 140:25051.*
Kuboi et al, "Oxidative Refolding of Lysozyme Assisted by Negatively Charged Liposomes: Relationship With Lysozyme-Medicated Fusion of Liposomes" Journal of Bioscience and Bioengineering, vol. 90, p. 14-19 (2000).
Bogdanov et al, "Phospholipid-assisted Refolding of an Integral Membrane Protein" The Journal of Biological Chemistry, vol. 274, p. 12339-12345 (1999).
Kirsch et al, "Cloning, High-Yield Expression in *Escherichia Coli*, and Purification of Biologically Active HIV-1 Tat Protein" Protein Expression and Purification, vol. 8, p. 75-84 (1996).
Nath et al, "α-Crystallin and ATP Facilitate the In Vitro Renaturation of Xylanase: Enhancement of Refolding by Metal Ions" Protein Science, vol. 11, p. 2727-2734 (2002).
Seibutsu Kogaku Kaisha, Feb. 25, 2005, vol. 83, pp. 90.
Daisuke Nohara et al., "Media Selection for Refolding of Thermolysin by Use of Immobilized Preparation", Journal Bioscence & Bioengineering (2000), vol. 89, No. 2, pp. 188-192.
Irene Griswold-Prenner et al., Biochemistry, "G-Protein Effector Coupling . . . ", (1989), vol. 28, pp. 6145-6150.
Daisuke Nohara et al., "Media Selection for Refolding of Thermolysin by Use of Immobilized Preparation", Journal Bioscence & Bioengineering (2000), vol. 89, No. 2, pp. 188-192.
Irene Griswold-Prenner et al., Biochemistry, "G-Protein Effector Coupling . . . ", (1989), vol. 28, pp. 6145-6150.
Kagaku Dai-jiten, vol. 2, Compact Edition 19, p. 704 (partial translation) (Sep. 10, 1976).
Kagaku Dai-jiten, vol. 3, Compact Edition 19, p. 26 (partial translation) (Sep. 10, 1976).
Kagaku Dai-jiten, vol. 3, Compact Edition 19, p. 823 (partial translation) (Sep. 10, 1976).
Kagaku Dai-jiten, vol. 8, Compact Edition 19, p. 116 (partial translation) (Sep. 10, 1976).
Kagaku Dai-jiten, vol. 3, Compact Edition 19, p. 673 (partial translation) (Sep. 10, 1976).

* cited by examiner

*Primary Examiner*—Rei-tsang Shiao
(74) *Attorney, Agent, or Firm*—Dennison, Schultz & MacDonald

(57) ABSTRACT

A refolding agent and refolding method which make it possible to produce high-purity proteins in high productivity. The refolding agent includes a phosphorus-containing compound (A) and an oxycarbonyl group-containing compound (B). The refolding method includes the step of treating the unfolded protein with the refolding agent. As the compound (A), there may be mentioned at least one species selected from inorganic phosphoric acids, alkyl phosphate esters, sugar phosphate esters, and salts of these, and as the compound (B), there may be mentioned at least one species selected from formic acid, acetic acid, propionic acid, lactic acid, tartaric acid, and salts of these.

7 Claims, No Drawings

PROTEIN REFOLDING AGENT AND REFOLDING METHOD

TECHNICAL FIELD

The present invention relates to a protein refolding agent and a protein refolding method and, more particularly, to a refolding agent to be used for refolding an unfolded protein to an active protein structure, and a method of such refolding.

BACKGROUND ART

It is very important to elucidate and analyze the function and structure of a protein, since it may be directly connected with the treatment of a disease or the creation of a new drug, for instance. Therefore, intensive studies have been made for synthesizing or producing various proteins by various methods, examining the structures thereof, and elucidating the mechanisms of action and the roles thereof in living organisms. It is now well known that the function of a protein is decided not only by the sequence of amino acids constituting the protein and the chain length but also by an orderly three-dimensional structure (higher order structure) it exhibits.

From the industrial viewpoint as well, the advancement of genetic engineering has made it possible to mass-produce various recombinant proteins for the use thereof in a wide range of industries, for example in drug manufacture, food processing and clinical diagnosis. Further, the development of the vector technology has made it possible for the technology of mass-producing target proteins in such microorganisms as *Escherichia coli* and yeasts to be practiced in a simple and easy manner using small amounts of resources and with good reproducibility.

However, many of the proteins expressed in recombinants are not orderly in three-dimensional structure or not controlled in higher order structure but often form inactive small-particle granules called inclusion bodies. Therefore, in production processes using *Escherichia coli*, a procedure is necessary for unfolding such inclusion bodies and converting them to soluble proteins having an orderly three-dimensional structure by higher order structure modification, namely for unfolding inclusion bodies and further refolding unfolded protein molecules.

This kind of refolding is applicable not only to proteins produced in *Escherichia coli* or yeasts but also to the regeneration of proteins inactivated by a certain cause, for example by thermal hysteresis; thus, it is a very important technology. Therefore, in the art, intensive studies have been made of this refolding technology and various methods have been proposed. However, the methods are mostly low in refolding rate; in addition, in many cases, favorable results were obtained incidentally with certain limited proteins (in particular specific low-molecular-weight proteins). Up to now, this refolding technology has not yet matured into a general and universal one which is applicable to various proteins, is efficient and economical, and gives high refolding rates.

Dialysis and dilution are old procedures used for refolding. The dialysis method comprises subjecting a protein to dialysis to refold the protein to its functional three-dimensional structure by gradually diluting a protein denaturing agent (unfolding agent; e.g. guanidine hydrochloride and/or urea) added in advance and substituting a buffer or the like therefor. Known as an example of application of this method is the stepwise dilution method which can raise the yield of refolding a protein to its functional three-dimensional structure by more slowly lowering the protein denaturing agent concentration (e.g. Non-Patent Document 1).

However, the dialysis method is not practical from the industrial point of view since the required volume of the dialyzing fluid generally amounts to at least 100 times the volume of the protein solution and, further, a period of several days is required.

The dilution method is widely used since it can be finished in a relatively short period of time and the volume required is relatively small, as compared with the dialysis method. The dilution method comprises excessively diluting, with a buffer or the like, a solution of a protein unfolded by addition of a protein denaturing agent (unfolding agent) to thereby refold the protein from its unfolded state to its functional three-dimensional structure. While the dilution method is a most simple and low-cost method of refolding a protein to its functional three-dimensional structure, the refolding yield rate is low (e.g. Non-Patent Document 2) and the high dilution ratio leads to a low yield under the existing circumstances.

An attempt has also been made to use an adsorptive separation column for refolding. When a protein or thioredoxin unfolded with urea/guanidine hydrochloride is subjected to gel filtration, refolding thereof occurs during gel filtration (Non-Patent Document 3). However, this method cannot always give sufficiently high refolding rates; generally, no satisfactory results can be obtained with other proteins. It has further been reported that when a protein solubilized with 8 M urea is adsorbed on a column with the molecular chaperone GroEL, a kind of protein promoting the refolding of a structurally denatured protein, immobilized thereon and then eluted with a solution containing 2 M potassium chloride and 2 M urea, refolding of the eluted protein occurs (Non-Patent Document 4). However, such refolding is observed only with a very limited number of proteins, for example cyclophilin A. In particular, under the present conditions, the use of a molecular chaperone, which is a certain kind of template, cannot serve at all when the protein to be refolded is incompatible with the template.

In some cases, a metal chelate is used as a substance to be immobilized on a column in lieu of the refolding promoting protein. When a His6tag-fused protein unfolded with an aqueous solution containing guanidine hydrochloride and urea is adsorbed on a resin with a nickel chelate immobilized thereon and the column is then washed with an unfolding agent-free buffer, refolding of the fused protein occurs (Non-Patent Document 5). However, the situation is the same: this method is applicable only to such protein and the resin preparation is complicated and results in increased costs.

There are also reports saying that when β-cyclodextrin or cycloamylose is used as an artificial chaperone and a protein unfolded with a surfactant is added to a solution of such chaperone, the surfactant is removed in the manner of inclusion in the artificial chaperone and, in this process, the protein is refolded (Non-Patent Document 6 to 8). However, such method is successfully applicable only to carbonic anhydrase B and the like. Furthermore, the method cannot be carried out repeatedly; hence, it is an expensive method.

In spite of such various proposed methods of refolding as discussed above, problems are still encountered in refolding unfolded proteins, namely low yields resulting from high-ratio dilution of the proteins as well as low purity levels.

Non-Patent Document 1: J. Biol. Chem. 2003 Mar. 14; 278(11):8979-8987

Non-Patent Document 2: J. Immunol. Methods. 1998 Oct. 1; 219(1-2):119-129

Non-Patent Document 3: Biochemistry, Vol. 26 (1987) 3135-3141

Non-Patent Document 4: Natl. Acad. Sci. USA, Vol. 94 (1997) 3576-3578

Non-Patent Document 5: Life Science News (Japan Ed.) Vol. 3 (2001) 6-7

Non-Patent Document 6: J. Am. Chem. Soc. Vol. 117 (1995) 2373-2374

Non-Patent Document 7: J. Biol. Chem. Vol. 271 (1996) 3478-3487

Non-Patent Document 8: FEBS Lett. Vol. 486 (2000) 131-135

SUMMARY OF THE INVENTION

The present inventors made intensive investigations to solve the problems mentioned above and, as a result, they have now completed the present invention.

Thus, the present invention relates to a refolding agent for an unfolded protein which is a phosphorus-containing refolding agent (C) comprising a compound (A) having a group represented by the general formula (1) given below;

a refolding agent for an unfolded protein which is an oxycarbonyl group-containing refolding agent (D) comprising a compound (B) having at least one group selected from the group consisting of carboxyl group, carboxylate anion group and ester groups;

a method of refolding an unfolded protein which comprises using, in the step of treating the unfolded protein with the above-mentioned refolding agent (C) or (D) comprising the compound (A) or compound (B) (refolding step), the refolding agent (C) at a compound (A) concentration, in the system, of 0.2 to 6 moles/L or the refolding agent (D) at a compound (B) concentration, in the system, of 0.01 to 6 moles/L;

a method of protein production which comprises the step of refolding by the method mentioned above; and a protein obtained by the production method mentioned above.

DETAILED DESCRIPTION OF THE INVENTION

The refolding agent according to the invention is an agent for refolding an unfolded protein and broadly includes two main groups, namely phosphorus-containing refolding agents (C) and oxycarbonyl group-containing refolding agents (D).

Thus, it includes phosphorus-containing refolding agents (C) characterized by comprising a compound (A) having a group represented by the general formula (1) given below and oxycarbonyl group-containing refolding agents (D) characterized by comprising a compound (B) having at least one group selected from the group consisting of carboxyl group, carboxylate anion group and ester groups.

In the refolding step, the phosphorus-containing refolding agent (C) is used preferably at a compound (A) concentration, in the system, of 0.2 to 6 moles/L and the oxycarbonyl group-containing refolding agent (D) is used preferably at a compound (B) concentration, in the system, of 0.01 to 6 moles/L.

Among the refolding agents according to the invention, the phosphorus-containing refolding agent (C) is characterized by its comprising a compound (A) having a group represented by the general formula (1) given below.

In the above general formula (1), P represents a phosphorus atom and, as the compound (A), there may be mentioned inorganic phosphoric acids and salts thereof (A1); alkyl phosphate esters and salts thereof (A2); and sugar phosphate esters and salts thereof (A3), among others.

As the inorganic phosphoric acids and salts thereof (A1), there may be mentioned phosphoric acid, hypophosphorous acid, phosphorous acid, hypophosphoric acid, pyrophosphoric acid, pyrophosphorous acid, metaphosphoric acid, tripolyphosphoric acid, polyphosphoric acids (tetrapolyphosphoric acid, hexapolyphosphoric acid, etc.) and salts of these.

As the salts, there may be mentioned alkali metal salts (sodium salt, potassium salt, lithium salt), alkaline earth metal salts (calcium salt, magnesium salt, barium salt, etc.), ammonium salt, amine salts (primary amine salts, secondary amine salts, tertiary amine salts) and quaternary ammonium salts (tetraalkylammonium salts etc.), among others.

As specific examples of the salts among (A1), there may be mentioned phosphoric acid salts such as disodium hydrogenphosphate, sodium dihydrogenphosphate, dipotassium hydrogenphosphate, potassium dihydrogenphosphate, ammonium phosphate, tetramethylammonium phosphate, tetraethylammonium phosphate, triethylamine phosphate and triethanolamine phosphate; phosphorous acid salts such as sodium phosphite, potassium phosphate, ammonium phosphate, tetramethylammonium phosphite, tetraethylammonium phosphite, triethylamine phosphite and triethanolamine phosphite; pyrophosphoric acid salts such as sodium pyrophosphate, potassium pyrophosphate, tetramethylammonium pyrophosphate, tetraethylammonium pyrophosphate, triethylamine pyrophosphate and triethanolamine pyrophosphate; and tripolyphosphoric acid salts such as sodium tripolyphosphate, potassium tripolyphosphate and tetraethylammonium tripolyphosphate.

As the alkyl phosphate esters and salts thereof (A2), there may be mentioned alkyl phosphate esters (A21), alkyl pyrophosphate esters (A22) and alkyl tripolyphosphate esters (A23), each having an alkyl group containing 1 to 12 carbon atoms, as well as salts thereof.

As the alkyl phosphate esters (A21) having an alkyl group containing 1 to 12 carbon atoms, there may be mentioned methyl phosphate, ethyl phosphate, propyl phosphate, 2-propyl phosphate, butyl phosphate, 2-butyl phosphate, tert-butyl phosphate, pentyl phosphate, hexyl phosphate, cyclohexyl phosphate, octyl phosphate, nonyl phosphate, decyl phosphate, dodecyl phosphate and the like.

As the alkyl pyrophosphate esters (A22) having an alkyl group containing 1 to 12 carbon atoms, there may be mentioned methyl pyrophosphate, ethyl pyrophosphate, propyl pyrophosphate, 2-propyl pyrophosphate, butyl pyrophosphate, 2-butyl pyrophosphate, tert-butyl pyrophosphate, pentyl pyrophosphate, hexyl pyrophosphate, cyclohexyl pyrophosphate, octyl pyrophosphate, nonyl pyrophosphate, decyl pyrophosphate, dodecyl pyrophosphate and the like.

As the alkyl tripolyphosphate esters (A23) having an alkyl group containing 1 to 12 carbon atoms, there may be mentioned methyl tripolyphosphate, ethyl tripolyphosphate, propyl tripolyphosphate, 2-propyl tripolyphosphate, butyl tripolyphosphate, 2-butyl tripolyphosphate, tert-butyl tripolyphosphate, pentyl tripolyphosphate, hexyl tripolyphosphate, cyclohexyl tripolyphosphate, octyl tripolyphosphate, nonyl tripolyphosphate, decyl tripolyphosphate, dodecyl tripolyphosphate and the like.

As the salts of the above-mentioned (A21) to (A23), there may be mentioned, among others, the same alkali metal salts, alkaline earth metal salts, ammonium salt, amine salts and quaternary ammonium salts as enumerated hereinabove referring to the compounds (A1).

As the sugar esters and salts thereof (A3), there may be mentioned, among others, adenosine triphosphate (ATP), adenosine diphosphate (ADP), adenosine monophosphate (AMP) and cyclic adenosine monophosphate (c-AMP) as well as the sodium, potassium, triethylamine and triethanolamine salts thereof.

From the refolding effect viewpoint, the compounds (A1) and (A3) are preferred among the phosphorus-containing compounds (A), and phosphoric acid, pyrophosphoric acid, polyphosphoric acids, adenosine triphosphate, adenosine diphosphate, adenosine monophosphate, and salts of these are more preferred.

Among the refolding agents according to the invention, the oxycarbonyl group-containing refolding agent (D) is characterized by its comprising a compound (B) having at least one group selected from the group consisting of carboxyl group, carboxylate anion group and ester groups.

Each compound (B) is characterized by its containing an oxycarbonyl group (—COO—) within the molecular thereof.

As the compound (B), there maybe mentioned compounds (B1) having at least one carboxyl group (—COOH) or at least one carboxylate anion group (—COO$^-$) within the molecule thereof and compounds (B2) having at least one ester group (—COOR) within the molecule thereof. The compound (B) further includes hydroxy carboxylic acids having an oxycarbonyl group and a hydroxyl group simultaneously, for example lactic acid.

As the compounds (B1) having at least one carboxyl group or carboxylate anion group, there may be mentioned the following carboxylic acids and ether carboxylic acids as well as salts thereof.

As the carboxylic acids among the compounds (B1), there may be mentioned aliphatic carboxylic acids (B11) containing 1 to 36 carbon atoms (including the carbonyl group carbon atom; hereinafter, the same shall apply) and aromatic carboxylic acids (B12).

As the aliphatic carboxylic acids (B11), there may be mentioned saturated aliphatic monocarboxylic acids containing 1 to 36 carbon atoms (formic acid, acetic acid, propionic acid, butyric acid, isobutyric acid, valeric acid, caproic acid, enanthic acid, caprylic acid, pelargonic acid, lauric acid, myristic acid, stearic acid, behenic acid, 2-ethylhexanoic acid, etc.); unsaturated aliphatic monocarboxylic acids containing 3 to 36 carbon atoms (acrylic acid, methacrylic acid, oleic acid, etc.); aliphatic hydroxy carboxylic acids containing 3 to 36 carbon atoms (glycolic acid, lactic acid, tartaric acid, gluconic acid, etc.); saturated aliphatic dicarboxylic acids containing 2 to 36 carbon atoms (oxalic acid, malonic acid, succinic acid, glutaric acid, adipic acid, pimelic acid, suberic acid, azelaic acid, sebacic acid, etc.) and monoalkyl esters thereof; unsaturated aliphatic dicarboxylic acids containing 4 to 36 carbon atoms (maleic acid, fumaric acid, itaconic acid, etc.); and at least tribasic (preferably tri-to dodecabasic) aliphatic polycarboxylic acids (citric acid, butanetetracarboxylic acid, cyclopentanetetracarboxylic acid, ethylenediaminetetraacetic acid, diethylenetriaminepentaacetic acid, etc.) among others.

As the aromatic carboxylic acids (B12), there may be mentioned aromatic monocarboxylic acids containing 7 to 36 carbon atoms (benzoic acid, cinnamic acid, hydroxybenzoic acid, etc.); aromatic dicarboxylic acids containing 8 to 36 carbon atoms (phthalic acid, isophthalic acid, terephthalic acid, etc.); aromatic tricarboxylic acids and tetracarboxylic acids containing 9 to 36 carbon atoms (trimellitic acid, pyromellitic acid, etc.); and aromatic hydroxy carboxylic acids (salicylic acid etc.), among others.

As other carboxylic acids, there may be mentioned polymers at least one constituent monomer of which is selected from among the above-mentioned unsaturated aliphatic mono- or dicarboxylic acids, for example polyacrylic acid, polymaleic acid, acrylic acid/alkyl acrylate copolymers: number average molecular weight 500 to 50,000), among others.

As further carboxylic acids, there may be mentioned, for example, partial alkyl (containing 1 to 12 carbon atoms) esters of the above-mentioned dicarboxylic acids or at least tribasic polycarboxylic acids, for example monomethyl oxalate, monomethyl succinate, monomethyl maleate, monoethyl oxalate, monomethyl citrate, dimethyl citrate and the like.

As the ether carboxylic acids among the compound (B1), there may be mentioned compounds represented by the general formula (2) given below.

$$R^1-O-(R^2O)_p-R^3-COOH \quad (2)$$

(In the above formula, $R^1$ represents a hydrocarbon group containing 1 to 36 carbon atoms, $R^2$ represents an alkylene group containing 2 to 4 carbon atoms, $R^3$ represents an alkylene group containing 1 to 3 carbon atoms and p represents an integer of 1 to 50.)

$R^1$ is a hydrocarbon group containing 1 to 36 carbon atoms and includes, among others, a methyl group, an ethyl group, an n-propyl group, a 2-propyl group, an n-butyl group, a 2-butyl group, a tert-butyl group, a pentyl group, an n-hexyl group, a cyclohexyl group, an octyl group, a nonyl group, a decyl group and a dodecyl group. A part of $R^1$ may be substituted by a hydroxyl group.

$R^2$ is an alkylene group containing 2 to 4 carbon atoms and includes, among others, an ethylene group, a 1,2-propylene group, a 1,3-propylene group, a 1,2-butylene group and a 1,4-butylene group.

$R^3$ is an alkylene group containing 1 to 3 carbon atoms and includes a methylene group, an ethylene group, a 1,2-propylene group and a 1,3-propylene group.

p is an integer of 1 to 50, preferably 1 to 20, more preferably 1 to 10, particularly preferably 1 to 4.

As specific examples of the ether carboxylic acids, there may be mentioned polyoxyethylene hexyl ether carboxylic acids, polyoxyethylene octyl ether carboxylic acids, polyoxyethylene nonyl ether carboxylic acids, polyoxyethylene decyl ether carboxylic acids, polyoxyethylene decyl hydroxy ether carboxylic acids, polyoxyethylene dodecyl ether carboxylic acids, polyoxypropylene hexyl ether carboxylic acids, polyoxypropylene octyl ether carboxylic acids, polyoxypropylene nonyl ether carboxylic acids, polyoxypropylene decyl ether carboxylic acids, polyoxypropylene dodecyl ether carboxylic acids and the like.

The ether carboxylic acids can be produced by reacting high alcohols with monochlorocarboxylic acids.

As the compounds having a carboxylate anion group among the compound (B1), there may be mentioned salts of the above-mentioned carboxylic acids or ether carboxylic acids.

As the salts, there may be mentioned the same alkali metal salts, alkaline earth metal salts, ammonium salt, amine salts and quaternary ammonium salts as enumerated hereinabove referring to the compounds (A1).

As specific examples of the carboxylic acid salts, there may be mentioned salts of the above-mentioned saturated aliphatic monocarboxylic acids containing 1 to 36 carbon atoms (sodium formate, ammonium formate, guanidium formate, sodium acetate, ammonium acetate, guanidium acetate, sodium propionate, ammonium propionate, guanidium propionate, sodium butyrate, sodium caproate, etc.); salts of the unsaturated aliphatic monocarboxylic acids containing 3 to 36 carbon atoms (sodium acrylate etc.); salts of the aliphatic hydroxy carboxylic acids containing 3 to 36 carbon atoms (sodium glycolate, sodium lactate, ammonium lactate, guanidium lactate, sodium tartrate, potassium tartrate, ammonium tartrate, guanidium tartrate, sodium gluconate, etc.); salts of the saturated aliphatic dicarboxylic acids containing 2 to 36 carbon atoms (sodium oxalate, sodium succinate, sodium glutarate, etc.); salts of the unsaturated aliphatic dicarboxylic acids containing 4 to 36 carbon atoms (sodium maleate etc.); and salts of the partial alkyl esters of the above-mentioned dicarboxylic acids or at least tribasic polycarboxylic acids (sodium monomethyl oxalate, sodium monomethyl succinate, potassium monomethyl maleate, sodium monoethyl oxalate, sodium monomethyl citrate, sodium dimethyl citrate, etc.), among others.

As the ether carboxylic acid salts, there may be mentioned sodium polyoxyethylene hexyl ether carboxylates, sodium polyoxyethylene octyl ether carboxylates, sodium polyoxyethylene nonyl ether carboxylates, sodium polyoxyethylene decyl ether carboxylates, sodium polyoxyethylene decyl hydroxy ether carboxylates, sodium polyoxyethylene dodecyl ether carboxylates, sodium polyoxypropylene hexyl ether carboxylates, sodium polyoxypropylene octyl ether carboxylates, sodium polyoxypropylene nonyl ether carboxylates, sodium polyoxypropylene decyl ether carboxylates, sodium polyoxypropylene dodecyl ether carboxylates and the like.

As the compounds (B2) having at least one ester group within the molecule, there may be mentioned carboxylic acid alkyl esters (B21) and carboxylic acid-alkylene oxide adducts (B22), among others.

As the carboxylic acids constituting the carboxylic acid alkyl esters (B21), there may be mentioned the same carboxylic acids as enumerated hereinabove referring to the compounds (B1) having at least one carboxyl group or carboxylate anion group within the molecule.

As the alkyl group in the alkyl ester group, there may be mentioned straight or branched aliphatic alkyl groups containing 1 to 12 carbon atoms, such as a methyl group, an ethyl group, an n-propyl group, a 2-propyl group, an n-butyl group, a 2-butyl group, a tert-butyl group, a pentyl group, an n-hexyl group, a cyclohexyl group, an octyl group, a nonyl group, a decyl group and a dodecyl group.

As specific examples of the carboxylic acid alkyl esters (B21), there may be mentioned monocarboxylic acid alkyl esters (methyl formate, methyl acetate, ethyl formate, ethyl acetate, n-butyl acetate, methyl stearate, n-butyl stearate, etc.); dicarboxylic acid alkyl esters (dimethyl oxalate, dimethyl succinate, dimethyl maleate, diethyl oxalate, diethyl succinate, dimethyl adipate, etc.); and at least tribasic aliphatic polycarboxylic acids with all the carboxyl groups being esterified (trimethyl citrate, tetramethyl ethylenediaminetetraacetate, etc.).

As the carboxylic acid-alkylene oxide adducts (B22), there may be mentioned, among others, products of addition of 1 to 50 moles of an alkylene oxide containing 2 to 4 carbon atoms to the carboxylic acids mentioned hereinabove referring to the compounds (B1).

As the alkylene oxide, there may be mentioned ethylene oxide (hereinafter abbreviated as "EO"), propylene oxide (hereinafter abbreviated as "PO") and butylenes oxide, among others.

As specific examples of the carboxylic acid-alkylene oxide adducts, there may be mentioned monocarboxylic acid-EO adducts (formic acid-EO (1 to 10 moles) adducts, acetic acid-EO (1 to 10 moles) adducts, propionic acid-EO (1 to 10 moles) adducts, butyric acid-EO (1 to 10 moles) adducts, caproic acid-EO (2 to 20 moles) adducts, lauric acid-EO (1 to 20 moles) adducts, etc.); hydroxy carboxylic acid-EO adducts (glycolic acid-EO (1 to 20 moles) adducts, lactic acid-EO (1 to 20 moles) adducts, tartaric acid-PO (1 to 5 moles) adducts, etc.); aliphatic polycarboxylic acid-EO adducts (oxalic acid-EO (1 to 20 moles) adducts, malonic acid-EO (1 to 20 moles) adducts, succinic acid-EO (1 to 20 moles) adducts, glutaric acid-EO (1 to 20 moles) adducts, citric acid-EO (1 to 20 moles) adducts, maleic acid-EO (1 to 20 moles) adducts, etc.); and aromatic carboxylic acid-EO adducts (phthalic acid-EO (1 to 30 moles) adducts, terephthalic acid-EO (1 to 30 moles) adducts, etc.), among others.

From the refolding effect viewpoint, the compounds (B1) having a carboxyl group or carboxylate anion group are preferred among those compounds (B); more preferred are the aliphatic carboxylic acids (B11), in particular aliphatic carboxylic acids containing 1 to 8 carbon atoms, for example formic acid, acetic acid, propionic acid, lactic acid and tartaric acid, and salts thereof.

The refolding agents (C) or (D) may further contain, in addition to the compound (A) or (B), water and/or the surfactant (E), pH adjusting agent (F) and/or protein stabilizing agent (G) mentioned later herein, among others, according to need.

In the case of addition of water, the amount thereof to be added is not particularly restricted but is preferably 100 to 10,000 parts by weight, more preferably 200 to 5,000 parts by weight, per 100 parts by weight of the compound (A) or (B) added.

The "unfolded protein" so referred to herein may be a protein unfolded by any means. Preferred from the refolding effect viewpoint is a protein unfolded with guanidine hydrochloride, urea or a combination of these, in particular a protein unfolded in an aqueous solution containing guanidine hydrochloride or/and urea generally at a (total) concentration of not lower than 0.5 mole/L.

In cases where the protein is a protein containing an S—S bond within the molecule, the protein may be unfolded with the unfolding agent comprising guanidine hydrochloride and/or urea in the presence of such a reducing agent as 2-mercaptoethanol, dithiothreitol, cystine or thiophenol as added to the unfolding agent.

The unfolding agent may contain water and the like according to need.

As the protein species to be unfolded, there may be mentioned the same ones as the proteins given later herein (enzymes, recombinant proteins, nucleic acids, etc.).

In the practice of the invention, the unfolded protein preferably has a molecular weight of 1,000 to 300,000, more preferably from the refolding effect viewpoint, 10,000 to 250,000.

Generally, there is a correlation between the magnitude of the molecular weight and the difficulty in refolding and it is said that proteins having a high molecular weight (about 10,000 or higher) are very difficult to refold. The refolding method according to the invention is superior in refolding effect and, therefore, is a very effective method of refolding high-molecular-weight proteins having a molecular weight of 10,000 or higher as well.

Since proteins having a molecular weight lower than 1,000 can be refold with ease, the refolding method according to the invention is particularly effective in refolding proteins having a molecular weight of 1,000 or higher. When the molecular weight exceeds 300,000, the solubility in water tends to decline significantly.

The molecular weight of a protein can be measured by common techniques of gel electrophoresis.

The refolding method according to the invention is a method of refolding an unfolded protein and comprises the step of treating the unfolded protein with the above-mentioned refolding agent in which step the phosphorus-containing refolding agent (C) is generally used at a compound (A) concentration, in the system, of 0.2 to 6 moles/L and, in the case of the oxycarbonyl group-containing refolding agent (D), it is generally used at a compound (B) concentration, in the system, of 0.01 to 6 moles/L.

The phrase "in the system" as used herein referring to the concentration of each compound means the total amount of the refolding agent and unfolding agent used (including optional components in each agent). The amount of the protein used is generally small, hence is not included in "the system".

In the case of a phosphorus-containing refolding agent (C), the compound (A) concentration in the system is generally not lower than 0.2 mole/L, preferably not lower than 0.3 mole/L, still more preferably not lower than 0.5 mole/L. Within such concentration range, the effect of refolding the unfolded protein structure to the normal structure can be produced effectively.

When the compound (A) concentration is below 0.2 mole/L, the refolding effect (rate at which the unfolded protein can be refolded) is not remarkable.

When the concentration of the phosphorus-containing compound (A) according to the invention in the system is 0.2 mole/L or higher, an equilibrium concentration is presumably arrived at to facilitate the hydrogen bond formation between the group represented by the formula (1) given hereinabove and the protein.

While common phosphoric acid type compounds (e.g. phosphoric acid/sodium phosphate) are sometimes used as buffering agents in the prior art refolding steps, these buffering agents are used generally at a concentration of 0.02 mole/L or below, at most 0.05 mole/L and no refolding effect is observable at such concentration.

A phosphorus-containing compound (A) concentration in the system exceeding 6 moles/L tends to cause an increase in the viscosity of the system, making it difficult to separate and purify the protein in the subsequent protein production step; hence, such concentration is unfavorable.

In the case of the oxycarbonyl group-containing refolding agent (D), the effect of refolding the unfolded protein structure to the normal structure can be produced effectively when the compound (B) concentration in the system is not lower than 0.01 mole/L, preferably not lower than 0.02 mole/L, still more preferably not lower than 0.1 mole/L.

When the compound (B) concentration is below 0.01 mole/L, the refolding effect (rate at which the unfolded protein can be refolded) is not remarkable.

When the concentration of the compound (B) according to the invention in the system is 0.01 mole/L or higher, an equilibrium concentration is presumably arrived at to facilitate the hydrogen bond formation between the hydroxycarbonyl group and the protein.

A compound (B) concentration in the system exceeding 6 moles/L tends to cause an increase in the viscosity of the system, making it difficult to separate and purify the protein in the subsequent protein production step; hence, such concentration is unfavorable.

The "step of treating the unfolded protein with the refolding agent" so referred to herein is the step of mixing, with stirring, the unfolded protein with the refolding agent until there is no more heterogeneity; it further includes a certain subsequent period of allowing the mixture to stand, where necessary, for causing the refolding to proceed more sufficiently. The period of standing is not particularly restricted but, for example, is 1 to 50 hours. The temperature in the treatment step is not particularly restricted but, for example, is 4 to 30° C.

In carrying out the refolding method according to the invention, a surfactant (E) may further be used in the step of treatment with the refolding agent. Thus, a surfactant (E) may further be added, as an optional component, to the refolding agent.

The surfactant (E) includes such nonionic surfactants, cationic surfactants, anionic surfactants and amphoteric surfactants as given below. The addition of a surfactant is preferred from the prevention of protein aggregation viewpoint.

As the nonionic surfactants, there may be mentioned higher alcohol-alkylene oxide (hereinafter "alkylene oxide" is abbreviated as "AO") adducts [C8-24 higher alcohol (e.g. decyl alcohol, dodecyl alcohol, coco alkyl alcohol, octadecyl alcohol, oleyl alcohol)-EO (1 to 20 moles) adducts etc.], C6-24 alkyl-containing alkylphenol-AO adducts, polypropylene glycol-EO adducts and polyethylene glycol-PO adducts, Pluronic type surfactants, fatty acid-AO adducts and polyhydric alcohol type nonionic surfactants, among others.

As the cationic surfactants, there may be mentioned quaternary ammonium salt type cationic surfactants and amine salt type cationic surfactants.

As the anionic surfactants, there may be mentioned ether carboxylic acids and salts thereof, sulfuric acid esters and salts thereof, ether sulfuric acid esters and salts thereof, sulfonic acid salts, sulfosuccinate salts, fatty acid salts, acylated amino acid salts, and nature-derived carboxylic acids and salts thereof (e.g. chenodeoxycholic acid, cholic acid, deoxycholic acid), each having a hydrocarbon group containing 8 to 24 carbon atoms.

As the amphoteric surfactants, there may be mentioned betaine type amphoteric surfactants and amino acid type amphoteric surfactants.

In addition to those mentioned above, the surfactant (E) further includes those surfactants described in Japanese Patent Publication (Kokoku) Sho57-39678.

From the viewpoint of weak interaction with the protein, the surfactant (E) to be used in carrying out the refolding method according to the invention is preferably a nonionic surfactant.

The nonionic surfactant is not particularly restricted but includes such commercially available ones as Tween 20, Tween 40, Tween 60, Tween 80, Triton X-100 and Triton X-300, among others.

In cases where a surfactant (E) is added, the level of addition thereof is generally not higher than 20% by weight relative to 100% by weight of the level of addition of (A); from the refolding effect viewpoint, it is preferably 0.001 to 20% by weight, more preferably 0.01 to 5% by weight.

Where a surfactant (E) is added, the level of addition thereof relative to 100% by weight of the level of addition of (B) is generally not higher than 20% by weight; from the refolding effect viewpoint, it is preferably 0.001 to 20% by weight, more preferably 0.01 to 5% by weight.

In carrying out the refolding method according to the invention, a pH adjusting agent (F) and/or a protein stabilizing agent (G) may further be used in the step of treatment with the refolding agent. Thus, a pH adjusting agent (F) and/or a protein stabilizing agent (G) may be added, as an optional component, to the refolding agent.

As the pH adjusting agent (F), there may be mentioned Tris (N-tris (hydroxymethyl)methylaminoethanesulfonic acid), HEPES (N-2-hydroxyethylpiperazine-N'-2-ethanesulfonic acid) and phosphate buffers (e.g. aqueous solutions containing disodium hydrogenphosphate+hydrochloric acid, aqueous solutions containing sodium dihydrogenphosphate+sodium hydroxide), among others.

Where a phosphate buffer is used, the phosphate buffer comprises a phosphoric acid salt, so that there is an overlap thereof with a part of the phosphorus-containing compounds (A) according to the invention. When a phosphate buffer overlapping the compound (A) is used, the concentration of the compound (A) in the system is calculated regarding the phosphoric acid salt in the phosphate buffer as being included in the compound (A).

As already mentioned hereinabove, however, the upper limit to the concentration of a phosphate buffer added for the purpose of pH adjustment is at most 0.05 mole/L and, in cases where the phosphorus-containing compound (A) as the refolding agent according to the invention and a phosphate buffer for pH adjustment are used in combination, the concentration, in the system, of the compound (A) alone, excluding the phosphate buffer, is preferably 0.2 to 5.95 moles/L.

The refolding procedure is generally carried out at pH 7 to 8 and, in cases where a pH adjusting agent (F) is added, the level of addition thereof is not particularly restricted provided that the pH is adjusted to a level within that range. Generally, however, that level per 100% by weight of the amount of the compound (A) added is generally not higher than 20% by weight; from the refolding effect viewpoint, it is preferably 0.001 to 20% by weight, more preferably 0.01 to 20% by weight.

In the case of addition of a pH adjusting agent (F), the addition level thereof per 100% by weight of the compound (B) added is generally not higher than 20% by weight; from the refolding effect viewpoint, it is preferably 0.001 to 20% by weight, more preferably 0.01 to 20% by weight.

As the protein stabilizing agent (G), there may be mentioned reducing agents, polyols, metal ions and chelating reagents, among others.

As the reducing agents, there may be mentioned 2-mercaptoethanol, dithiothreitol, ascorbic acid, reduced form glutathione and cysteine, among others.

As the polyols, there may be mentioned glycerol, glucose, sucrose, ethylene glycol, sorbitol and mannitol, among others.

As the metal ions, there may be mentioned divalent metal ions such as a magnesium ion, a manganese ion and a calcium ion, among others.

As the chelating reagents, there may be mentioned ethylenediaminetetraacetic acid (EDTA) and glycol ether-diamine-N,N,N',N'-tetraacetic acid (EGTA), among others.

In cases where a protein stabilizing agent (G) is added, the level of addition thereof per 100% by weight of the compound (A) added is generally not higher than 10% by weight and, from the refolding effect viewpoint, it is preferably 0.001 to 10% by weight, more preferably 0.01 to 5% by weight.

Where a protein stabilizing agent (G) is added, the level of addition thereof per 100% by weight of the compound (B) added is generally not higher than 10% by weight and, from the refolding effect viewpoint, it is preferably 0.001 to 10% by weight, more preferably 0.01 to 5% by weight.

In carrying out the refolding method according to the invention, protein concentrations in the system which are higher than a certain level tend to cause increases in system viscosity and decreases in enzyme activity. Meanwhile, the production efficiency depends on the product of the protein concentration in the system multiplied by this enzyme activity, with the result that in the low system protein concentration range, the production efficiency depends on the protein concentration in the system but the production efficiency decreases in a high concentration range exceeding a certain level. Consequently, from the protein production efficiency viewpoint, the protein concentration in the system is preferably 0.2 to 30 mg/mL, more preferably 0.2 to 20 mg/mL, particularly preferably 0.25 to 5 mg/mL.

The phrase "in the system" as used herein in defining the protein concentration means the total amount of the refolding agent and unfolding agent used (including optional components in each agent), as mentioned hereinabove. The amount of the protein used is generally small, hence is not included in "the system".

The levels of addition of the compounds (A) or (B) relative to the weight of the protein is preferably 5 to 2,000 parts per part of the protein; more preferably from the refolding effect viewpoint, it is 10 to 1,000 parts per part of the protein.

The method of protein production according to the invention is a protein production method comprising the step of refolding the protein by the refolding method described hereinabove.

The protein obtained by the protein production method according to the invention is higher in purity than the prior art products since it is obtained by the above-mentioned refolding method; further, since no large-scale dilution is required, the protein can be obtained in high yields.

The protein production method according to the invention comprises, for example, the following order of steps.

(1) Step of protein production by cultivation: to cultivate a protein producer, such as *Escherichia coli*, to produce an enzyme or recombinant protein.
(2) Lysing step: to take out inclusion bodies from inside protein producer cells by using a lysing agent or the like.
(3) Unfolding step: to add an unfolding agent, at a level not lower than 0.5 mole/L, to a suspension of inclusion bodies (e.g. 10 mg protein/mL), if necessary followed by further addition of a reducing agent at a level not higher than 20 millimoles/L, further followed by gentle stirring and allowing the mixture to stand at room temperature for several hours.
(4) Refolding step: to add the refolding agent (C) or (D) to the unfolded protein-containing suspension and, after gentle stirring, allow the mixture to stand overnight at room temperature to effect refolding.

(5) Separation/isolation step: to separate and isolate the desired normal protein from the suspension by column chromatography, for instance.

As the protein producer in the above-mentioned step (1) of protein production by cultivation, there may be mentioned the following bacterial cells and other cells.

Thus, mention may be made of bacterial cells such as streptococci, staphylococci and cells belonging to the genus *Escherichia*, *Streptomyces* or *Bacillus*, eukaryotic cells such as yeast cells and cells belonging to the genus *Aspergillus*, insect cells such as *Drosophila* S2 cells and *Spodoptera* Sf9 cells, animal cells such as CHO, COS, HeLa, C127, 3T3, BHK, 293 and Bows melanoma cells, and plant cells, among others.

Among them, as specific examples of strains of the genus *Escherichia*, there may be mentioned *E. coli* K12DH1 [cf. Proc. Natl. Acad. Sci. USA, vol. 60, page 160 (1968)], JM103 [cf. Nucleic Acids Research, vol. 9, page 309 (1981)], JA221 [cf. Journal of Molecular Biology, vol. 120, page 517 (1978)], HB101 [cf. Journal of Molecular Biology, vol. 41, page 459 (1969)], C600 [cf. Genetics, vol. 39, page 440 (1954)] and MM294 [cf. Nature, vol. 217, page 1110 (1968)].

As specific examples of strains of the genus *Bacillus*, there may be mentioned *Bacillus subtilis* MI114 [cf. Gene, vol. 24, page 255 (1983)] and 207-21 [cf. Journal of Biochemistry, vol. 95, page 87 (1984)].

An expression vector containing a cDNA coding for the desired protein, which is to be used in recombinant protein production by cultivation, can be produced by:
(i) separating messenger RNA (mRNA) from cells producing the desired protein, synthesizing a single-stranded cDNA from the mRNA, then synthesizing the corresponding double-stranded DNA and inserting the complementary DNA into a phage or plasmid,
(ii) transforming a host with the recombinant phage or plasmid obtained in the above manner and, after cultivation, isolating the phage or plasmid containing the desired DNA by hybridization with a DNA probe coding for a part of the desired protein or by the immunoassay technique using an antibody, and
(iii) excising the desired cloned DNA from the recombinant DNA and joining the cloned DNA or a part thereof to an expression vector at a site downstream from an appropriate promoter therein.

Thereafter, a host is transformed with the thus-obtained expression vector by an appropriate method and then cultivated. The cultivation is generally carried at 15 to 43° C. for 3 to 24 hours, with aeration and/or stirring, if necessary.

The lysis in the lysing step can be carried out, for example, in the manner of physical disruption using ultrasonic waves, treatment with a lytic enzyme such as lysozyme, or treatment with a lysing agent such as a surfactant. From the productivity viewpoint, treatment with an lysing agent is preferred and, from the viewpoint of avoiding the degeneration of the useful protein, treatment with such a lysing agent as a quaternary ammonium type cationic surfactant whose counter ion is a carboxylic acid ion derived from formic acid or acetic acid, for instance, is particularly preferred.

The unfolding agent to be used in the unfolding step is, for example, guanidine hydrochloride, urea or a combination of these, as mentioned hereinabove.

In cases where the protein is a protein containing an S—S bond within the molecule, 2-mercaptoethanol, dithiothreitol, cystine or thiophenol, for instance, may further be added as a reducing agent in addition to guanidine hydrochloride and/or urea.

As the packing material to be used in column chromatography in the protein separation/isolation step, there may be mentioned silica, dextran, agarose, cellulose, polyacrylamide, vinyl polymers and the like, including such commercially available products as Sephadex series, Sephacryl series and Sepharose series products (all from Pharmacia), and Bio-Gel series products (from Bio-Rad), among others.

The protein according to the invention is a protein obtained by the above-mentioned protein production method.

The protein obtainable by the protein production method according to the invention includes enzymes, recombinant proteins and nucleic acids, among others.

As the enzymes, there may be mentioned hydrolases, isomerases, oxidoreductases, transferases, synthases and lyases, among others.

As the hydrolases, there may be mentioned proteases, serine proteases, amylases, lipases, cellulases and glucoamylase, among others.

As the isomerases, there may be mentioned glucose isomerase and the like.

As the oxidoreductases, there may be mentioned peroxidases, among others.

As the transferases, there may be mentioned acyl transferases and sulfotransferases, among others.

As the syntheses, there may be mentioned fatty acid syntheses, phosphate syntheses and citrate synthase, among others.

As the lyases, there may be mentioned pectin lyases and the like.

As the recombinant proteins, there may be mentioned protein preparations and vaccines, among others.

As the protein preparations, there may be mentioned interferon α, interferon β, interleukins 1 to 12, growth hormone, erythropoietin, insulin, granulocyte colony-stimulating factor (G-CSF), tissue plasminogen activator (TPA), natriuretic hormone, blood coagulation factor VIII, somatomedin, glucagon, growth hormone-releasing factor, serum albumin and calcitonin, among others.

As the vaccines, there may be mentioned hepatitis A vaccines, hepatitis B vaccines and hepatitis C vaccines, among others.

As the nucleic acids, there may be mentioned deoxyribonucleic acids (DNAs) and ribonucleic acids (RNAs).

EFFECT OF THE INVENTION

When the refolding agent and refolding method according to the invention are used, the productivity is increased dramatically as compared with the prior art since no large scale protein dilution is required. In addition, since the refolding effect is higher than in the prior art, it is possible to obtain high-purity proteins in large amounts.

BEST MODE FOR CARRYING OUT THE INVENTION

The following examples further illustrate the present invention. They are, however, by no means limitative of the scope of the invention. Proteins were obtained by carrying out the refolding procedures by the methods described in the following examples and comparative examples. The enzyme activity of each protein obtained was measured for productivity evaluation.

EXAMPLE 1

A 10-mg portion of lipase ("Rhilipase", product of Nagase ChemteX) and 1 ml of a 6 moles/L aqueous solution of guanidine hydrochloride (product of Wako Pure Chemical Industries) were added to a sterilized 10-ml test tube, and the mixture was allowed to stand overnight at room temperature for unfolding the lipase.

To the thus-unfolded protein-containing solution was added 5 ml of 1.2 moles/L solution of a phosphate mixture (A-1) (disodium hydrogenphosphate:sodium dihydrogenphosphate=1:1 (mole ratio) (both being products of Wako Pure Chemical Industries)) and the mixture was allowed to stand overnight at room temperature for refolding (the compound (A-1) concentration in the system=1.0 mole/L; the protein concentration in the system in the refolding step=1.7 mg/ml).

EXAMPLE 2

The same refolding procedure as in Example 1 was followed except that 1.2 moles/L sodium tripolyphosphate (product of Wako Pure Chemical Industries) (A-2) was used in lieu of the 1.2 moles/L phosphate mixture (A-1) (the compound (A-2) concentration in the system=1.0 mole/L; the protein concentration in the system in the refolding step=1.7 mg/ml).

EXAMPLE 3

The same refolding procedure as in Example 1 was followed except that 1.2 moles/L sodium adenosine monophosphate (product of SIGMA) (A-3) was used in lieu of the 1.2 moles/L phosphate mixture (A-1) (the compound (A-3) concentration in the system=1.0 mole/L; the protein concentration in the system in the refolding step=1.7 mg/ml).

EXAMPLE 4

The same refolding procedure as in Example 1 was followed except that 1.2 moles/L sodium adenosine triphosphate (product of SIGMA) (A-4) was used in lieu of the 1.2 moles/L phosphate mixture (A-1) (the compound (A-4) concentration in the system=1.0 mole/L; the protein concentration in the system in the refolding step=1.7 mg/ml).

EXAMPLE 5

The same refolding procedure as in Example 1 was followed except that the concentration of 5 ml of phosphate mixture (A-1) was changed from 1.2 moles/L to 0.6 mole/L (the compound (A-1) concentration in the system=0.5 mole/L; the protein concentration in the system in the refolding step=1.7 mg/ml).

EXAMPLE 6

The same refolding procedure as in Example 1 was followed except that the concentration of 5 ml of phosphate mixture (A-1) was changed from 1.2 moles/L to 6 mole/L (the compound (A-1) concentration in the system=5.0 mole/L; the protein concentration in the system in the refolding step=1.7 mg/ml).

EXAMPLE 7

The same refolding procedure as in Example 1 was followed except that 5 ml of 0.3 mole/L sodium tripolyphosphate (A-2) was used in lieu of the 1.2 moles/L phosphate mixture (A-1) (the compound (A-2) concentration in the system=0.25 mole/L; the protein concentration in the system in the refolding step=1.7 mg/ml).

EXAMPLE 8

The same refolding procedure as in Example 1 was followed except that the concentration of 5 ml of phosphate mixture (A-1) was changed from 1.2 moles/L to 6.7 moles/L (the compound (A-1) concentration in the system=5.6 moles/L; the protein concentration in the system in the refolding step=1.7 mg/ml).

EXAMPLE 9

The same refolding procedure as in Example 1 was followed except that the amount of lipase was changed from 10 mg to 1.7 mg (the compound (A-1) concentration in the system=1.0 mole/L; the protein concentration in the system in the refolding step=0.28 mg/ml).

EXAMPLE 10

The same refolding procedure as in Example 1 was followed except that the amount of lipase was changed from 10 mg to 27 mg (the compound (A-1) concentration in the system=1.0 mole/L; the protein concentration in the system in the refolding step=4.5 mg/ml).

EXAMPLE 11

The same refolding procedure as in Example 1 was followed except that 5 ml of 1.2 moles/L sodium formate (product of Wako Pure Chemical Industries) (B-1) was used in lieu of the 1.2 moles/L phosphate mixture solution (A-1) (the compound (B-1) concentration in the system=1.0 mole/L; the protein concentration in the system in the refolding step=1.7 mg/ml).

EXAMPLE 12

The same refolding procedure as in Example 11 was followed except that the concentration of 5 ml of sodium formate (B-1) was changed from 1.2 moles/L to 0.24 mole/L (the compound (B-1) concentration in the system=0.2 mole/L; the protein concentration in the system in the refolding step=1.7 mg/ml).

EXAMPLE 13

The same refolding procedure as in Example 11 was followed except that 1.2 moles/L sodium acetate (product of Wako Pure Chemical Industries) (B-2) was added in lieu of the 1.2 moles/L sodium formate (B-1) (the compound (B-2) concentration in the system=1.0 mole/L; the protein concentration in the system in the refolding step=1.7 mg/ml).

EXAMPLE 14

The same refolding procedure as in Example 11 was followed except that 1.2 moles/L sodium propianate (product of Wako Pure Chemical Industries) (B-3) was added in lieu of the 1.2 moles/L sodium formate (B-1) (the compound (B-3) concentration in the system=1.0 mole/L; the protein concentration in the system in the refolding step=1.7 mg/ml).

EXAMPLE 15

The same refolding procedure as in Example 11 was followed except that 1.2 moles/L sodium citrate (product of Wako Pure Chemical Industries) (B-4) was added in lieu of the 1.2 moles/L sodium formate (B-1) (the compound (B-4) concentration in the system=1.0 mole/L; the protein concentration in the system in the refolding step=1.7 mg/ml).

EXAMPLE 16

The same refolding procedure as in Example 11 was followed except that 1.2 moles/L sodium monomethyl succinate (product of Wako Pure Chemical Industries) (B-5) was added in lieu of the 1.2 moles/L sodium formate (B-1) (the compound (B-5) concentration in the system=1.0 mole/L; the protein concentration in the system in the refolding step=1.7 mg/ml).

EXAMPLE 17

The same refolding procedure as in Example 11 was followed except that ether carboxylic acid (sodium polyoxyethylene (about 4.5 moles of EO) dodecyl ether carboxylate (product of Sanyo Chemical Industries, Ltd.: BEAULIGHT LCA-Na) (B-6)) was added in lieu of the 1.2 moles/L sodium formate (B-1) (the compound (B-6) concentration in the system=1.0 mole/L; the protein concentration in the system in the refolding step=1.7 mg/ml).

EXAMPLE 18

The same refolding procedure as in Example 11 was followed except that 1.2 moles/L ammonium formate (product of Wako Pure Chemical Industries) (B-7) was added in lieu of the 1.2 moles/L sodium formate (B-1) (the compound (B-7) concentration in the system=1.0 mole/L; the protein concentration in the system in the refolding step=1.7 mg/ml).

EXAMPLE 19

The same refolding procedure as in Example 11 was followed except that 1.2 moles/L ammonium acetate (product of Wako Pure Chemical Industries) (B-8) was added in lieu of the 1.2 moles/L sodium formate (B-1) (the compound (B-8) concentration in the system=1.0 mole/L; the protein concentration in the system in the refolding step=1.7 mg/ml).

EXAMPLE 20

The same refolding procedure as in Example 11 was followed except that 1.2 moles/L sodium lactate (product of Wako Pure Chemical Industries) (B-9) was added in lieu of the 1.2 moles/L sodium formate (B-1) (the compound (B-9) concentration in the system=1.0 mole/L; the protein concentration in the system in the refolding step=1.7 mg/ml).

EXAMPLE 21

The same refolding procedure as in Example 11 was followed except that 1.2 moles/L sodium tartrate (product of Wako Pure Chemical Industries) (B-10) was added in lieu of the 1.2 moles/L sodium formate (B-1) (the compound (B-10) concentration in the system=1.0 mole/L; the protein concentration in the system in the refolding step=1.7 mg/ml).

COMPARATIVE EXAMPLE 1

Refolding in the Case of the Concentration of Compound (A) in the System is Excessively Low The same refolding procedure as in Example 1 was followed except that the concentration of 5 ml of phosphate mixture (A-1) was changed from 1.2 moles/L to 0.22 mole/L (the compound (A-1) concentration in the system=0.18 mole/L; the protein concentration in the system in the refolding step=1.7 mg/ml).

COMPARATIVE EXAMPLE 2

Refolding in the Case of the Concentration of Compound (A) in the System is Excessively High The same refolding procedure as in Example 1 was followed except that the concentration of 5 ml of phosphate mixture (A-1) was changed from 1.2 moles/L to 7.4 moles/L (the compound (A-1) concentration in the system=6.2 moles/L; the protein concentration in the system in the refolding step=1.7 mg/ml).

COMPARATIVE EXAMPLE 3

Refolding in the Case of the Concentrations of Compound (A) snd Protein in the System are Excessively Low The same refolding procedure as in Example 1 was followed except that the concentration of 5 ml of phosphate mixture (A-1) was changed from 1.2 moles/L to 0.22 mole/L, and the amount of lipase was changed to 1.1 mg (the compound (A-1) concentration in the system=0.18 mole/L; the protein concentration in the system in the refolding step=0.18 mg/ml).

COMPARATIVE EXAMPLE 4

Refolding in the Case of the Concentration of Compound (A) in the System is Low and the Concentration of Protein in the System is Excessively High The same refolding procedure as in Example 1 was followed except that the concentration of 5 ml of phosphate mixture (A-1) was changed from 1.2 moles/L to 0.22 mole/L, and the amount of lipase was changed to 192 mg (the compound (A-1) concentration in the system=0.18 mole/L; the protein concentration in the system in the refolding step=32.0 mg/ml).

COMPARATIVE EXAMPLE 5

Refolding in the Case of the Concentration of Compound (B) in the System is Excessively Low The same refolding procedure as in Example 11 was followed except that the concentration of 5 ml of sodium formate (B-1) was changed from 1.2 moles/L to 0.01 mole/L (the compound (B-1) concentration in the system=0.008 mole/L; the protein concentration in the system in the refolding step=1.7 mg/ml).

COMPARATIVE EXAMPLE 6

Refolding in the Case of the Concentration of Compound (B) in the System is Excessively High The same refolding procedure as in Example 11 was followed except that the concentration of 5 ml of sodium formate (B-1) was changed from 1.2 moles/L to 7.4 moles/L (the compound (B-1) concentration in the system=6.2 moles/L; the protein concentration in the system in the refolding step=1.7 mg/ml).

COMPARATIVE EXAMPLE 7

Refolding Using s Phosphate Buffer for pH Adjustment

The same refolding procedure as in Example 1 was followed except that 5 ml of commercial "1/15 mole/L phosphate buffer (pH=7) aqueous solution" (sodium phosphate buffer, product of Wako Pure Chemical Industries) was used in lieu of the 1.2 moles/L phosphate mixture (A-1) (the phosphate concentration in the system=0.06 mole/L; the protein concentration in the system in the refolding step=1.7 mg/ml).

COMPARATIVE EXAMPLE 8

Refolding by Means of Large-Scale Dilution Using a Phosphate Buffer for pH Adjustment Since no enzyme activity was found in Comparative Example 7, the dilution ratio was further increased as compared with Comparative Example 7 for improvement.

To a sterilized 10-ml test tube were added 10 mg of lipase [Rhilipase] and 1 ml of 6 mole/L aqueous solution of guanidine hydrochloride, and the mixture was allowed to stand overnight at room temperature for sufficient unfolding of the lipase.

The above enzyme solution (1 ml) and 200 mL of commercial "1/15 mole/L phosphate buffer (pH=7) aqueous solution" (sodium phosphate buffer, product of Wako Pure Chemical Industries) were placed in a sterilized 210-ml bottle and, after, gentle stirring, the mixture was allowed to stand overnight at room temperature for refolding (the phosphate concentration in the system=0.07mole/L; the protein concentration in the refolding step=0.05 mg/ml).

COMPARATIVE EXAMPLE 9

Refolding by Means of Large-Scale Dilution of the Sample Used in Comparative Example 1

Since the enzyme activity was low in Comparative Example 1 mentioned above, the dilution ratio was further increased as compared with Comparative Example 1 for improvement.

To a sterilized 10-ml test tube were added 10 mg of lipase [Rhilipase] and 1 ml of 6 mole/L aqueous solution of guanidine hydrochloride, and the mixture was allowed to stand overnight at room temperature for sufficient unfolding of the lipase.

The above enzyme solution (1 ml) and 200 mL of 0.18 mole/L sodium phosphate buffer (pH=7) were placed in a sterilized 210-ml bottle and, after, gentle stirring, the mixture was allowed to stand overnight at room temperature for refolding (the phosphate concentration in the system=0.18 mole/L; the protein concentration in the refolding step=0.05 mg/ml).

COMPARATIVE EXAMPLE 10

Refolding (1) by a Dilution Method

The same refolding procedure as in Comparative Example 8 was followed except that 200 mL of 0.1 mole/L Tris buffer (tris hydroxyaminomethane buffer, product of Wako Pure Chemical Industries) (pH=7) was used in lieu of the commercial "1/15 mole/L phosphate buffer (pH=7) aqueous solution" (the protein concentration in the system in the refolding step=0.05 mg/ml).

COMPARATIVE EXAMPLE 11

Refolding (2) by a Dilution Method

To a sterilized 10-ml test tube were added 10 mg of lipase [Rhilipase] and 1 ml of 6 mole/L aqueous solution of guanidine hydrochloride, and the mixture was allowed to stand overnight at room temperature for sufficient unfolding of the lipase.

The above enzyme solution (CTAB) (1 ml) and 70 ml of 0.05% cetyltrimethylammonium bromide (product of Tokyo Chemical Industry Co., Ltd.) solution were placed in a sterilized 140-ml bottle and, after the mixture was allowed to stand for 1 hour at room temperature, 30 ml of 2% cycloamylose (product of EZAKI GLICO CO., LTD.) solution was added thereto followed by overnight standing (the protein concentration in the refolding step=0.1 mg/ml).

COMPARATIVE EXAMPLE 12

Refolding by a Dialytic Method

To a sterilized 10-ml test tube were added 10 mg of lipase [Rhilipase] and 1 ml of 6 mole/L aqueous solution of guanidine hydrochloride, and the mixture was allowed to stand overnight at room temperature for sufficient unfolding of the lipase.

The above enzyme solution (1 ml) was placed in a dialyzer and gradually diluted with gradual addition of 0.1 mole/L Tris buffer (pH=7) for immediate refolding. The procedure was finished after addition of 200 ml of the Tris buffer (the protein concentration in the refolding step=0.05 mg/mL).

<Enzyme Activity Measurement>

To sterilized 10-ml test tubes, there were added 2 ml of 0.1 mole/L Tris buffer (pH=7) and 5 µl of each of the protein solutions obtained in Examples 1 to 21 and Comparative Examples 1 to 12, respectively, using a micropipette, followed by gentle stirring.

Further, 1 ml of a 3.5 millimoles/L p-nitrophenyl acetate solution was added to each test tube, and absorbance (400 nm) of the hydrolysis product p-nitrophenol was measured at 3-minute intervals for 12 minutes using an ultraviolet/visible spectrophotometer (product of Shimadzu, UV-2550), and the initial rate (Ka) of the hydrolysis reaction was calculated based on the rate of increase in absorbance with time.

Separately, aqueous solutions of "Rhilipase" respectively having the same concentrations as the protein concentrations in Examples 1 to 21 and Comparative Examples 1 to 12 were prepared and, for each of them, the initial rate (Kb) of the hydrolysis reaction of p-nitrophenyl acetate was calculated.

The enzyme activity (%) in each of the above-mentioned examples and comparative examples was calculated as follows:

Enzyme activity (%)=$(Ka/Kb) \times 100$

The enzyme activity represents the refolding rate.

<Protein Productivity Evaluation>

The protein productivity was defined as the following indicator and evaluated (in the table, rounded off to the nearest whole number).

Productivity=protein concentration (mg/mL) in system in refolding step×enzyme activity (%)

The enzyme activity and productivity data for the above-mentioned examples and comparative examples are shown in Table 1.

TABLE 1

| | Example | | | | | | | | | | | | | | | | | | | | |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 |
| Compound (A) concentration in system (moles/L) | 1.0 | 1.0 | 1.0 | 1.0 | 0.5 | 5.0 | 0.25 | 5.6 | 1.0 | 1.0 | — | — | — | — | — | — | — | — | — | — | — |
| Compound (B) concentration in system (moles/L) | — | — | — | — | — | — | — | — | — | — | 1.0 | 0.2 | 1.0 | 1.0 | 1.0 | 1.0 | 1.0 | 1.0 | 1.0 | 1.0 | 1.0 |
| Protein concentration in system in refolding step (mg/mL) | 1.7 | 1.7 | 1.7 | 1.7 | 1.7 | 1.7 | 1.7 | 1.7 | 0.28 | 4.5 | 1.7 | 1.7 | 1.7 | 1.7 | 1.7 | 1.7 | 1.7 | 1.7 | 1.7 | 1.7 | 1.7 |
| Evaluation results — Enzyme activity (%) | 60 | 80 | 30 | 40 | 60 | 50 | 70 | 50 | 70 | 20 | 40 | 35 | 45 | 40 | 30 | 30 | 25 | 60 | 60 | 45 | 40 |
| Evaluation results — Productivity (%) | 102 | 136 | 51 | 68 | 102 | 85 | 119 | 85 | 20 | 90 | 68 | 60 | 77 | 68 | 51 | 51 | 43 | 102 | 102 | 77 | 68 |

| | Comparative Example | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Compound (A) concentration in system (moles/L) | 0.18 | 6.2 | 0.18 | 0.18 | — | — | 0.06 | 0.07 | 0.18 | — | — | — |
| Compound (B) concentration in system (moles/L) | — | — | — | — | 0.008 | 6.2 | — | — | — | — | — | — |
| Tris buffer concentration in system (moles/L) | — | — | — | — | — | — | — | — | — | 0.1 | — | 0.1 |
| CTAB concentration in system (%) | — | — | — | — | — | — | — | — | — | — | 0.05 | — |
| Protein concentration in system in refolding step (mg/mL) | 1.7 | 1.7 | 0.18 | 32.0 | 1.7 | 1.7 | 1.7 | 0.05 | 0.05 | 0.05 | 0.1 | 0.05 |
| Evaluation results — Enzyme activity (%) | 5 | 5 | 5 | 0 | 5 | 5 | 0 | 20 | 30 | 15 | 60 | 15 |
| Evaluation results — Productivity (%) | 9 | 9 | 1 | 0 | 9 | 9 | 0 | 1 | 2 | 1 | 6 | 1 |

INDUSTRIAL APPLICABILITY

When the refolding agent and refolding method according to the invention are used, it is possible to efficiently obtain various useful proteins in high-purity.

The protein obtainable by the protein production method according to the invention includes enzymes, recombinant proteins and nucleic acids, among others.

The invention claimed is:

1. A method of refolding an unfolded protein which comprises the step of treating the unfolded protein with an oxycarbonyl-containing refolding agent (D) comprising a compound (B), the compound (B) is selected from at least one species selected from the group consisting of formic acid, acetic acid, propionic acid, lactic acid, tartaric acid, citric acid, succinic acid, ether carboxylic acid represented by the general formula (2) given below, and the salts of these, $$R^1\text{—O—}(R^2O)_p\text{—}R^3\text{—COOH} \quad (2)$$

where, in the general formula (2), $R^1$ represents a hydrocarbon group containing 1 to 36 carbon atoms, $R^2$ represents an alkylene group containing 2 to 4 carbon atoms, $R^3$ represents an alkylene group containing 1 to 3 carbon atoms, and p represents an integer of 1 to 50, wherein, in this step, the concentration thereof at the compound (B) concentration, in the system, is 0.01 to 6 moles/L.

2. The method according to claim 1 a surfactant (E) may further be used in the step of treating with the refolding agent.

3. The method according to claim 1 wherein a pH adjusting agent (F) and/or protein stabilizing agent (G) is used in the step of treating with the refolding agent.

4. The method according to claim 1 wherein, in the step of treating with the oxycarbonyl-containing refolding agent (D), the protein concentration in the system is 0.2 to 30 mg/mL.

5. A method of protein production which comprises the step of refolding by the method according to claim 1.

6. The method according to claim 1 wherein the unfolded protein has a molecular weight of 1,000 to 300,000.

7. The method according to claim 1 wherein the unfolded protein is a protein unfolded with guanidine hydrochloride and/or urea.

* * * * *